United States Patent [19]

Walker et al.

[11] 4,209,861
[45] Jul. 1, 1980

[54] JOINT PROSTHESIS

[75] Inventors: Peter S. Walker, Ridgewood; Rocco Borzone, Emerson, both of N.J.

[73] Assignee: Howmedica, Inc., New York, N.Y.

[21] Appl. No.: 880,057

[22] Filed: Feb. 22, 1978

[51] Int. Cl.² ............................................. A61F 1/24
[52] U.S. Cl. .................................. 3/1.911; 3/1.91; 128/92 C
[58] Field of Search ............................... 3/1.9–1.911; 128/92 C

[56] References Cited

U.S. PATENT DOCUMENTS

| 3,694,821 | 10/1972 | Moritz | 3/1.91 |
| 3,728,742 | 4/1973 | Averill et al. | 3/1.911 |
| 3,774,244 | 11/1973 | Walker | 3/1.911 |
| 3,798,679 | 3/1974 | Ewald | 3/1.91 |
| 3,813,700 | 6/1974 | Tavernetti et al. | 3/1.911 |
| 3,837,009 | 9/1974 | Walker | 3/1.911 |
| 3,840,905 | 10/1974 | Deane | 3/1.911 |
| 3,868,730 | 3/1975 | Kaufer et al. | 3/1.911 X |
| 3,869,729 | 3/1975 | Attenborough | 3/1.91 |
| 4,034,418 | 7/1977 | Jackson et al. | 3/1.911 |

FOREIGN PATENT DOCUMENTS

2452412  5/1976  Fed. Rep. of Germany ............ 3/1.911

Primary Examiner—Ronald L. Frinks
Attorney, Agent, or Firm—Pennie & Edmonds

[57] ABSTRACT

A novel knee prosthesis is disclosed comprising a femoral component and a tibial component adapted respectively to be secured to the adjacent ends of the femur and tibia, with each component comprising a spaced pair of bearing portions for articulation of the knee in the sagittal plane. A first guiding surface carried by the femoral component cooperates with a second guiding surface carried by the tibial component to induce posterior movement of the contact area of the femoral bearing portions upon the tibial bearing portions with increasing flexion of the knee. The two guiding surfaces are preferably located in the intercondylar region. The prosthesis may also be adapted for use in other joints, e.g. the elbow.

17 Claims, 18 Drawing Figures

JOINT PROSTHESIS

BACKGROUND OF THE INVENTION

In the treatment of diseased or damaged human knee joints, particularly in cases of deterioration resulting from arthritis, surgical repair involving introduction of an artificial knee prosthesis is often required. Knee prostheses currently in use generally fall within one of two categories. First, in cases of relatively mild deterioration of the knee joint, condylar surface prostheses such as the ones disclosed in U.S. Pat. Nos. 3,728,742 and 3,774,244 are utilized. These prostheses comprise spaced pairs of artificial femoral and tibial condylar bearing portions adapted for mutual articulation. They afford substantial rotational and translational freedom of movement, are relatively light in weight, require only minor resection of natural bone for implantation, and do not require severance of the cruciate ligaments. The second category consists of hinge and ball-in-socket type devices which provide a direct linkage between the femoral and tibial components of the prosthesis. These devices are capable of providing considerable stability in cases where severe deterioration of the knee joint has occurred, but are considerably heavier and more restrictive than the prostheses of the first category and require greater resection of natural bone for implantation. Examples of prostheses in this second category include those disclosed in U.S. Pat. Nos. 3,837,009 and 3,868,730.

In cases of intermediate deterioration and instability, a need exists for a knee prosthesis that will combine the desirable features of the two categories of prostheses discussed above, i.e., the considerable freedom of rotational and translational movement, minimal resection of natural bone for implantation, and relatively light weight of the first category with the substantial degree of stability against undesired movement and dislocation provided by the linked type of prostheses.

Additionally, with knee prostheses in general, it is desirable to reduce the contact stresses and wear of the bearing portions upon each other. Excessive stress can distort the shape of the bearing portions, while excessive wear can cause the emission of significant quantities of prosthetic materials into the physiological system [see Swanson, S. and Freeman, M., "The Scientific Basis of Joint Replacement", John Wiley and Sons, Chapter 3 (1977)].

U.S. Pat. No. 3,840,905 discloses a prosthetic knee joint wherein the femoral and tibial components possess approximately saddle shapes, with the two components contacting one another in a substantially load-bearing intercondylar portion.

SUMMARY OF THE INVENTION

A novel joint prosthesis articulatable between extended and flexed positions has been devised, comprising a first component, a second component, a bearing portion in each of said components, the bearing portions of said components being in articulatable mutual contact over a contact area when in use, a guiding surface on each of said components, the guiding surfaces of said components being in mutual contact during at least a portion of the flexion of said joint from the extended to the flexed position, said guiding surfaces interacting during at least a substantial portion of the flexion of said joint to effect movement of said contact area, and said guiding surfaces being substantially non-load bearing. Although of particular interest as a knee prosthesis, with posterior movement of the contact area effected, the novel prosthesis may also be adapted for use in other joints, e.g. the elbow.

The invention comprises additionally a novel prosthetic knee joint articulatable between extended and flexed positions comprising a femoral component for securement to the knee end of the femur, a tibial component for securement to the end of the tibia adjacent the femur, each of said components having a pair of spaced bearing portions, the bearing portions of said components being in articulatable mutual contact over a contact area when in use, a post between the pair of bearing portions of one of said components, said post having a guiding surface, said post in use being received between the pair of bearing portions of the other of said components, said other component having a guiding surface between its pair of bearing portions, said guiding surfaces being in mutual contact during at least a portion of the flexion of said joint from the extended to the flexed position, and said guiding surfaces interacting during at least a substantial portion of the flexion of said joint to effect posterior movement of said contact area. The posterior movement of the contact area serves to distribute the load and wear on the tibial bearing portions, to prevent premature limitation of flexion caused by impingement of the femur against the posterior end of the tibial component, and to approximate the motion of the natural knee.

In one embodiment of the novel knee prosthesis, said post is carried by the tibial component and cooperates with an intercondylar box carried by the femoral component. This embodiment provides adequate stability in cases of moderate deterioration of the human knee, yet need not be as bulky or restrictive as the linked prostheses or require as great a removal of natural bone for implantation.

Another aspect of a novel knee prosthesis of the invention, concerning the shapes of the femoral and tibial bearing portions in the lateral direction, permits smoother varus-valgus movement in the prosthetic joint.

DETAILED DESCRIPTION OF THE INVENTION

The invention will be described in detail with reference to a preferred embodiment thereof, which is a knee prosthesis. Reference to this embodiment does not limit the scope of the invention, which is limited only by the scope of the claims.

In the drawings:

FIGS. 10 (a) to (f) are schematic cross-sections of the prosthesis of FIG. 1 showing six different relative positions of the mutually engaged femoral and tibial components, from full extension to full flexion of the knee;

Figure 9:
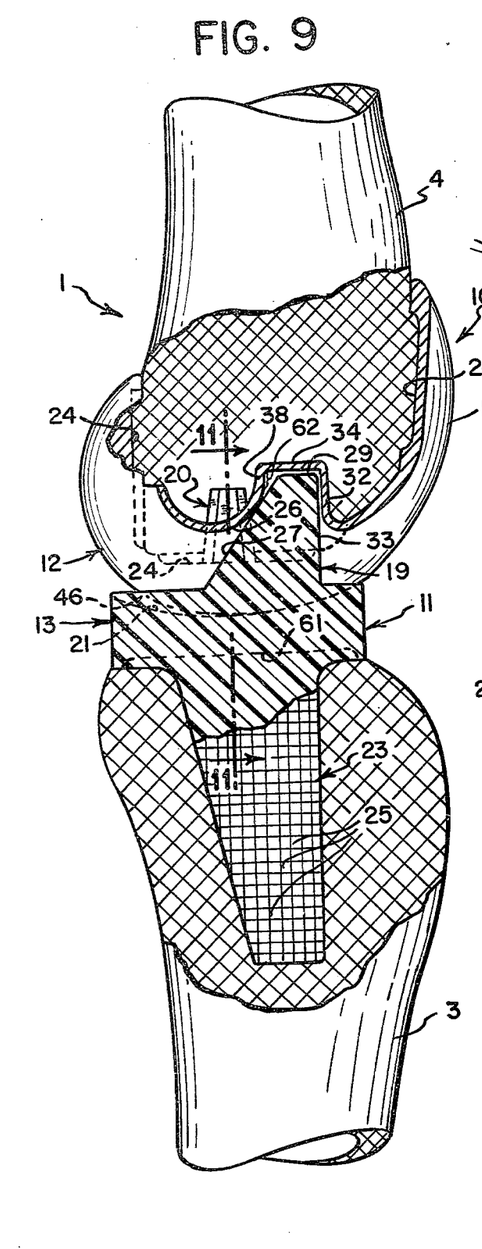
FIG. 9 is a cross-section taken along the center line of FIGS. 5 and 7 of the prosthesis of FIG. 1 showing the mutual engagement of the femoral and tibial components in the fully extended knee and the adjacent bone portions.
Figure 10A:
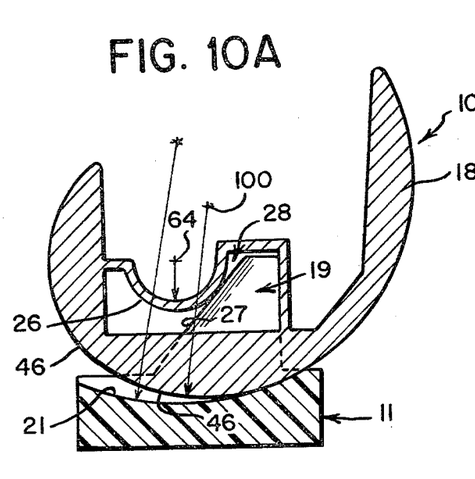
Figure 10B:
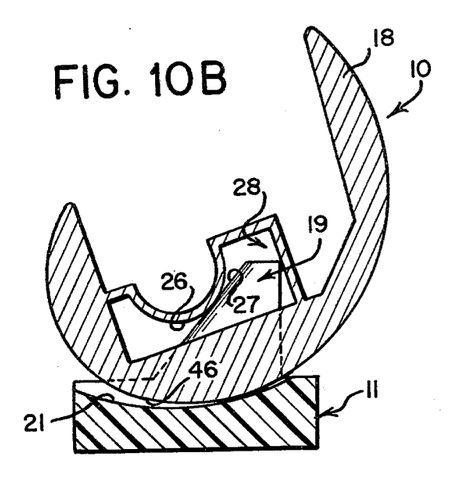
Figure 10C:
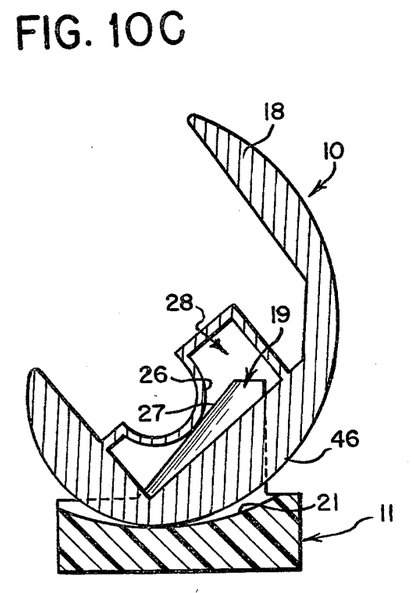
Figures 10D, 10E:
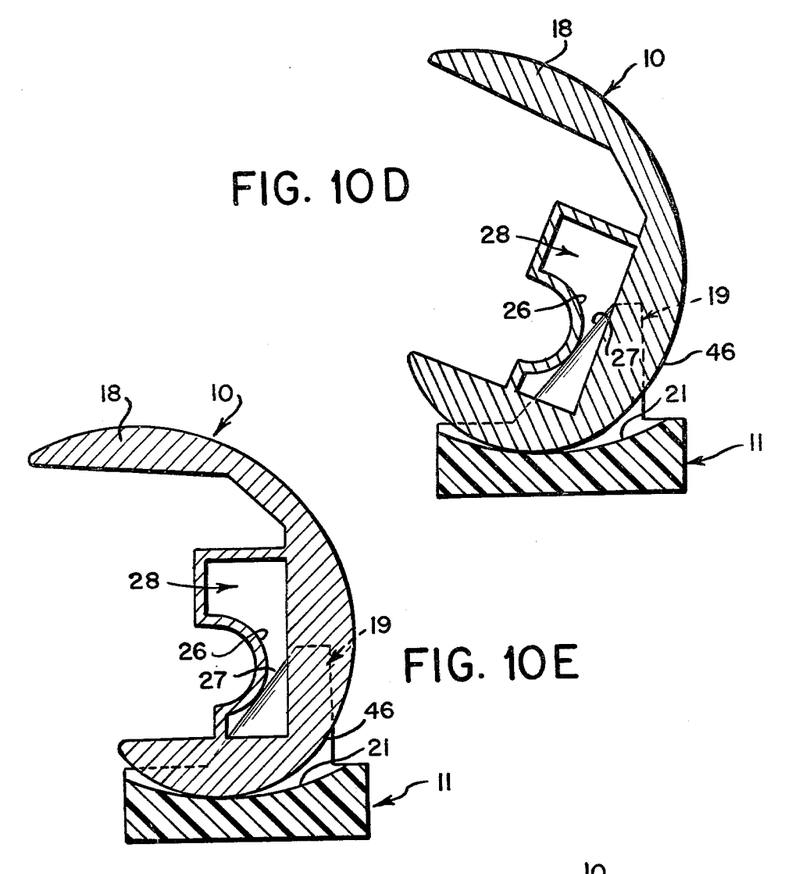
Figure 10F:
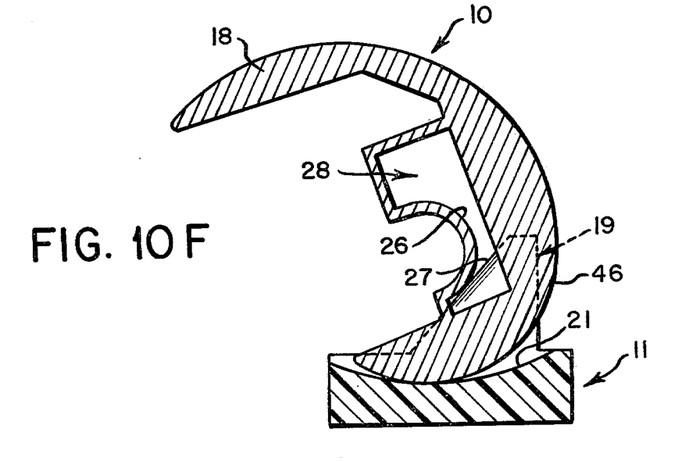

The femoral component 10 and tibial component 11 of a preferred embodiment of the invention 1 are shown in FIGS. 1 to 12. The anterior direction is to the right and the posterior direction to the left in FIGS. 2 and 9. The tibia 3 and femur 4 of the surgically repaired left knee joint are shown in FIG. 9. The cruciate ligaments of the knee joint will have been severed, but various other ligaments and tendons not shown in FIG. 9, e.g., the collateral ligaments, will generally be viable and remain in place.

Component 10 comprises a spaced pair of downwardly convex bearing portions 12 adapted for mutual articulation with mating bearing portions 13 of the tibial component 11, a first intercondylar guiding portion 14 disposed between and joining the two bearing portions 12, a bridging portion 16 joining the anterior ends of the two bearing portions 12 and the guiding portion 14, and a patellar flange 18 extending above the bridging portion 16 and adapted to receive the patella. Preferably, the patellar flanges of the left and right femoral components contain tracks 60 (see FIG. 4) on their anterior faces angled at about 6°, to the left and right respectively, to allow anatomical tracking of the patella. This is the only difference between the left and right femoral components of this preferred embodiment of the invention, and a fully symmetrical version with a non-angled patellar track is, of course, possible, as is elimination of flange 18. The external bearing surfaces 46 of the femoral bearing portions 12 exhibit a shape in sagittal planes, as viewed in FIGS. 2 and 9, similar to that of the natural femoral condyles, with the posterior part of said shape being an arc of a circle. Component 10 is preferably an integrally cast article of a metal surgical implant alloy, such as a cobalt-chromium base alloy or a stainless steel. Preferably, it is made of the cobalt-chromium base surgical implant alloy trademarked under the name Vitallium by Howmedica, Inc. (New York, N.Y.).

Component 10 is adapted to be secured to the condyles of the resected femur. Ribbed tapered pins 20 projecting upwardly from the inner faces of portions 12 are received within corresponding openings drilled into the femur. Ribs 22 provide a key to improve the fixation of component 10 to the femur by means of a cement such as polymethylmethacrylate. A key may also be made in the surfaces of the openings drilled into the femur. Additionally, component 10 is provided with recesses 24 on the inner surfaces of bearing portions 12 and patellar flange 18 which receive cement, cement grip pads, or, as an alternative, bone tissue ingrowth pads.

Figures 1, 2:
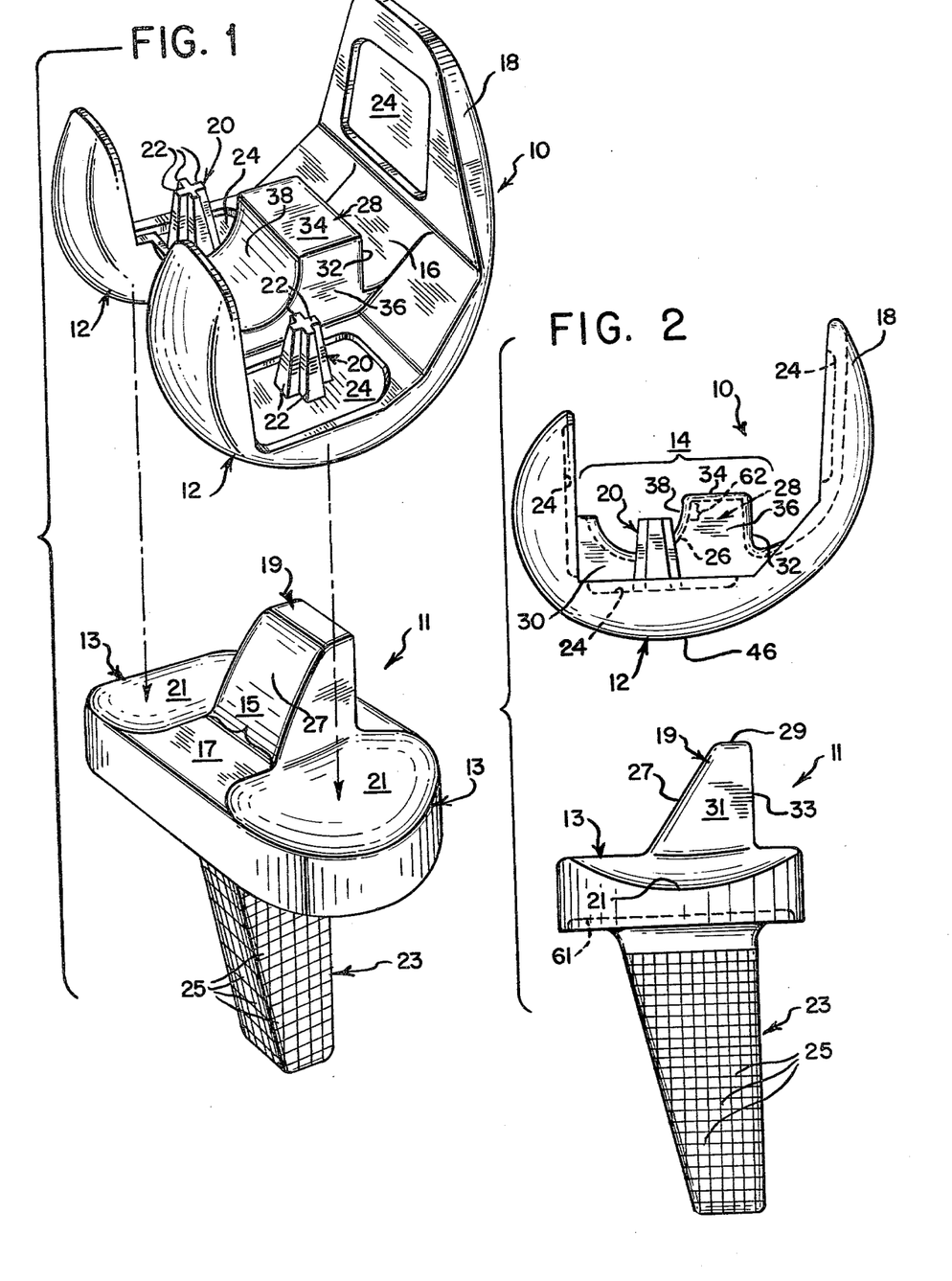
FIG. 1 is an exploded perspective of a left knee prosthesis of the invention showing femoral and tibial components.
FIG. 2 is an exploded side elevation of the prosthesis of FIG. 1.

The guiding portion 14 comprises a downwardly convex guiding surface 26 presented to the tibial component 11, an intercondylar box 28 open downwardly to component 11, and substantially posterior extensions 30 of the side walls 36 of box 28. The inner surface of box 28 is defined by anterior 32, top 34, side 36 and posterior 38 walls. As can be seen clearly in FIG. 2, the anterior face of guiding surface 26, i.e. that portion of surface 26 to the right of its lowest point in FIG. 2, coincides with the posterior wall 38 of box 28. The posterior wall 38 of box 28 extends a short distance 62 above the anterior end of surface 26, as is shown in FIG. 2, before reaching its junction with the top wall 34 of box 28.

Tibial component 11 comprises a spaced pair of upwardly concave bearing portions 13 adapted to receive the femoral bearing portions 12, and a second intercondylar guiding portion 15 disposed between and joining the two bearing portions 13. The left and right tibial components are interchangeable in this embodiment. The guiding portion 15 comprises a bridging portion 17 which directly joins the two bearing portions 13 throughout their length in the anterior/posterior direction, and an intercondylar post 19 adapted to be received in the intercondylar space of the femoral component 10. The shape of the external bearing surfaces 21 of bearing portions 13 in sagittal planes, as viewed in FIGS. 2, 9 and 10, closely coincides with the shape of the middle and anterior parts of bearing surfaces 46 of femoral bearing portions 12, so as to provide substantial load distribution in the extended artificial knee joint. This substantial similarity between the shapes in sagittal planes of the contacting surfaces 21 and 46 when the knee is extended is clearly seen in FIG. 9. Tibial component 11 is preferably constructed of a biologically compatible high density polymer such as high molecular weight polyethylene. Although it is preferred to have a metallic femoral component and a plastic tibial component, this relationship may be reversed so that the tibial component is metallic and the femoral component plastic. Additionally, other materials of construction may be used for either component, such as pyrolytic or vitreous carbon, or a ceramic material.

Component 11 is adapted to be secured to the upper extremity of the resected tibia. It is provided with a relatively long downward projecting peg 23 adapted to be received for cement fixation in a corresponding opening made by the surgeon in the upper extremity of the tibia. Grid 25 and recesses 61 are provided on the sides of peg 23 and the bottom of bearing portions 13, respectively, to receive cement, cement grip pads, or tissue ingrowth pads, and thus improve the fixation. Alternative methods of securing the tibial component to the resected upper extremity of the tibia may also be employed. For example, portions 13 and 15 may be received and supported by a metallic tibial tray, which may incorporate a downward projecting peg. The tibial tray may be affixed to the tibia by means of cement, tissue ingrowth or any other known means.

The operation of knee prosthesis 1 with femoral component 10 engaged with tibial component 11 is best explained with reference to FIGS. 9 and 10, which show cross-sections of the two engaged components at different stages of articulation from full extension to full flexion. Surface 26 cooperates with surface 27 at all stages, whether the knee is in extension or flexion, to prevent anterior movement (e.g. skidding) of the femoral component 10 with respect to the tibial component 11. Additionally, as is shown in FIG. 10, as flexion of the knee begins the convex guiding surface 26 engages the posterior surface 27 of the intercondylar post 19. Surfaces 26 and 27, being in contact, cooperate to induce posterior movement of the contact area of bearing portions 12 upon bearing portions 13 with increasing flexion of the knee. It is important to note that the intercondylar guiding portions 14 and 15 of the femoral and tibial components are substantially non-load bearing, with the great majority of the load being borne by the bearing portions 12 and 13. This is in contrast to the knee prosthesis disclosed in U.S. Pat. No. 3,840,905.

In the embodiment of FIGS. 1 to 12 the cross-sectional shape of surface 26 exhibited in sagittal planes is an arc of a circle subtending an angle of about 180°. As rendered in the actual article, the convex guiding surface 26 is a portion of the surface of a circular cylinder with the longitudinal axis of the cylinder the center of curvature of the convex guiding surface. Surface 27 which cooperates with surface 26 is sloped downwardly in the posterior direction. As is shown in an exaggerated manner in FIG. 10 (a), the center 64 of the arc defining surface 26 is offset in sagittal planes from the center 100 of the circular arc generally defining the posterior parts of surfaces 46 in sagittal planes. Thus, as the knee is flexed and component 10 shown successively in FIGS. 10a through 10e rotates counter-clockwise with respect to component 11, the contacting of eccentric surface 26 with surface 27 guides the contact area of the bearing surfaces 46 of the femoral bearing portions 12 posteriorally upon the bearing surfaces 21 of the tibial bearing portions 13. A desired rate of this posterior displacement with progressive flexion of the knee may be carefully controlled by the exact design of the configuration and disposition of surfaces 26, 27 and 46.

The scope of this aspect of the invention is not limited to the particular configurations of guiding surface 26, intercondylar post 19 and bearing surfaces 46 present in the embodiment of FIGS. 1 to 12. However, the configurations of these elements must be such that the contact between the convex guiding surface and the posterior surface of the intercondylar post induces posterior movement of the contact area of the femoral component upon the tibial component with increasing flexion of the knee. Thus, for example, the shape of guiding surface 26 exhibited in sagittal planes may be a curve centered at about the same point in sagittal planes as the circular arc generally defining the posterior parts of surfaces 46, with said curve being of increasing radius from its anterior to posterior end (i.e. a spiral). As the knee is flexed, the guiding surface 26, being, of course, in contact with the intercondylar pin 19, acts as a cam to guide the contact area of the femoral component 10 posteriorally upon the tibial component 11. The portion of the posterior surface 27 of post 19 which contacts guiding surface 26 need not always slope downwardly in the posterior direction as viewed in the sagittal plane. Thus, for example, the posterior surface of the intercondylar post may in certain situations coincide with a frontal plane. The downward/posterior sloping of surface 27 exemplified in FIGS. 1 to 12 is generally preferred however, especially when the distance between the part of surfaces 46 in contact with the tibial component 11 and the guiding surface 26 decreases as the knee is flexed. Such a decrease forces the contact point of the guiding surface 26 upon the post 19 to drop downward, and thus, where the surface 27 is sloped posteriorly and downwardly, the contact area of the surfaces 46 upon the surfaces 21 is forced in a posterior direction. The posterior surface of post 19 does not, of course, have to be planar. Finally, the bearing surfaces 46 of the femoral bearing portions 12 need not always have a similar shape in sagittal planes as the human femoral condyles, although it is preferred that they do. Thus, said bearing surfaces may in fact exhibit a circular shape in sagittal planes throughout their entire length from anterior to posterior end, with the backward guidance of their contact area with the tibial component effected, for example, by using an eccentric guiding surface 26 as described above. Alternatively, the femoral bearing surfaces may exhibit a spiral shape in sagittal planes, with decreasing radius from their anterior to posterior ends. The skilled worker in the art will recognize that many other possible combinations of the configurations of surfaces 26, 27 and 46 are possible that will achieve the backward guidance of the contact area of the bearing portions 12 upon the bearing portions 13 with increasing flexion of the artificial knee.

Additionally, whatever the configuration of the surfaces 26, 27 and 46 that is used to achieve the backward guidance of contact area described above, it is not necessary to fall within the scope of this aspect of the invention that the guiding portion 14 of the femoral component 10 contain an intercondylar box. Thus, for example, in FIG. 2, the walls 32, 34 and 36 may be eliminated or replaced with a different configuration that never comes into contact with the intercondylar post 19. Of course it is preferred that the guiding portion 14 contain an intercondylar box, such as box 28 in FIG. 2, in order to provide additional stability against undesired movements. In the broadest conception of the invention an intercondylar post is not necessary, only guiding surfaces carried respectively by the femoral and tibial components. The guiding surfaces need not always be disposed in the intercondylar regions of the components, and the guiding surface carried by the femoral component need not always be convex.

Although the bearing surfaces 21 of the tibial component 11 are generally concave upward in sagittal planes, a modification within the scope of the invention is to incorporate flattened regions into said surfaces 21 approximately at the middle of bearing portions 13 and somewhat posterior thereof, as viewed in sagittal planes. This provision of partially flattened surfaces affords an easier rolling of the femoral component upon the tibial component with flexion of the knee. Also, in order to reduce the wear of the convex guiding surface 26 upon the intercondylar pin 19, the surface 27 may be shaped to present a concave surface (viewed in sagittal planes) to the convex guiding surface 26, thus increasing the contact area between surfaces 26 and 27.

In the embodiment illustrated in FIGS. 1 to 12 the intercondylar box 28 is in loose sliding engagement with the intercondylar post 19 when the artificial knee is extended. That is, post 19 is not frictionally held within box 28. In the configuration shown in FIGS. 1 through 12, which is by no means limiting, the top 34, side 36 and anterior 32 walls of box 28 and the corresponding top 29, side 31 and anterior 33 surfaces of post 19 are substantially planar and orthogonal, with the anterior wall 32 and surface 33 being substantially parallel to frontal planes. The skilled worker in the art will note that other surfaces such as curved or slanted surfaces can be substituted for the planar orthogonal ones illustrated in FIGS. 1 to 12. Very small clearances exist between surface 27 and wall 38, between surface 29 and wall 34, and between surface 33 and wall 32 at full extension of the knee. The clearances between surfaces 31 and walls 36 are somewhat larger. The top wall 34 of box 28 cooperates with the top surface 29 of post 19 to prevent rotation of the tibia in the sagittal plane with respect to the femur substantially beyond full extension (i.e. clockwise rotation of the femur with respect to the tibia beyond the position shown in FIG. 9). Anterior wall 32 of box 28 cooperates with anterior surface 33 of post 19 to prevent posterior movement of femoral component 10 with respect to tibial component 11 when the knee is extended. As the artificial knee is flexed, however, and surfaces 26 and 27 become engaged, wall 32 lifts away from post 19 and thus does not interfere with the desired backward guidance of the femoral component 10 upon the tibial component 11 described above. Walls 36 and their extensions 30 cooperate with surfaces 31 of post 19 to limit lateral movement of the femoral component 10 with respect to the tibial component 11. It is, of course, desirable to provide some limited amount of lateral freedom of movement between components 10 and 11. Walls 38 and 32 of box 28 cooperate with surfaces 27 and 33 of post 19 to restrict rotation of the tibial component 11 with respect to the femoral component 10 about the longitudinal axis of the tibia when the knee is extended, but this restriction is reduced as the knee is flexed and wall 32 lifts away from surface 33. After a certain degree of flexion (about 45°) this restriction on rotational movement is removed altogether. The posteior surface 27 of post 19 may, of course, be substantially planar, but it is preferred that surface 27 be transversely convex to facilitate rotation of the tibial component with respect to the femoral component about the longitudinal axis of the tibia when the knee is not fully extended. In a further variation the convex guiding surface 26 may be rounded concavely in planes substantially longitudinal with respect to said surface so as to increase its contact area with a transversely convex posterior surface 27 of post 19, thus reducing the wear of the two surfaces upon each other.

Regardless of the exact design of the intercondylar post 19 or the intercondylar box 28, the interaction of the intercondylar guiding portions 14 and 15 provides, in addition to the desired backward guidance of the femoral component upon the tibial component with flexion of the knee, a highly desirable amount of stability against undesired movements and dislocations of the artificial knee, without at the same time causing the knee prosthesis to be unduly restrictive, cumbersome or uncomfortable in actual use in the body of the patient. The enhanced stability will compensate for the loss of the cruciate ligaments, which must be severed but have often already been rendered useless in cases of moderate deterioration of the natural knee joint such as that caused by arthritis.

Figure 13:
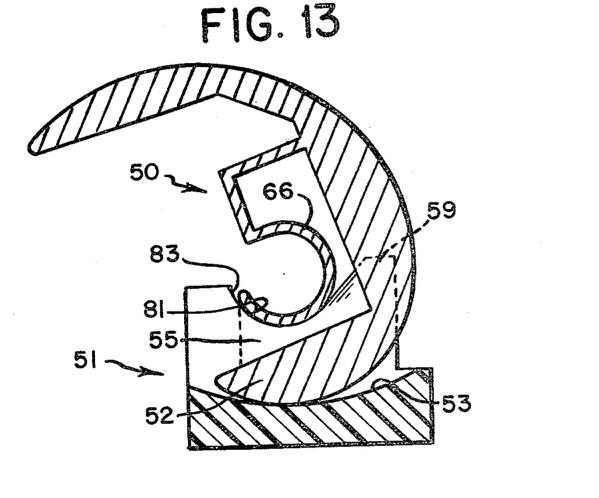
FIG. 13 is a schematic cross-sectional view (equivalent to FIG. 10 (f)) of a modified left knee prosthesis showing the mutual engagement of the femoral and tibial components in the fully flexed knee.

The femoral component 50 and tibial component 51 are shown for a modified knee prosthesis in FIG. 13. Use of this embodiment is most appropriate when further stability than that provided by the embodiment of FIGS. 1 to 12 is required. The second intercondylar guiding portion 55 comprises, in addition to intercondylar post 59 and a bridging portion joining the two bearing portions 53, a curved concave upward tibial trough 81 extending posteriorally from post 59 and adapted to receive the convex guiding surface 66 of the femoral component 50 so as to prevent posterior dislocation of femoral component 50 with respect to tibial component 51. The convex guiding surface 66 subtends an angle in sagittal planes of about 240° so that the posterior region of the upper surface 83 of trough 81 will come into contact with a curved convex surface if the artificial knee in flexion threatens to dislocate posteriorally. The radius of curvature of the upper surface 83 of trough 81 is sufficiently large so as not to interfere with the desired posterior movement with increasing flexion of the knee of the contact area of the femoral bearing portions 52 upon the tibial bearing portions 53. The means used to achieve this desired guided backward movement will generally be the same as described above for the embodiment of FIGS. 1 to 12. In an embodiment not shown, the convex guiding surface 66 subtends an angle of 360° and is thus equivalent to an axle carried by femoral component 50.

An additional aspect of the novel knee prosthesis of this invention (best shown in FIGS. 11 and 12) relates to the shape of the bearing surfaces 46 of the femoral bearing portions 12 in transverse sections through both of said bearing portions, and the corresponding bearing surfaces 21 of the tibial bearing portions 13 in transverse sections through both of said bearing portions, and the relationship of these shapes. This additional aspect of the invention is quite general and is not restricted to the embodiments of FIGS. 1 to 13 or to any other particular knee prosthesis design. The presence of an intercondylar post or an intercondylar box, for example, is not necessary. This aspect of the invention is applicable to any knee prosthesis comprising a femoral component and a tibial component, preferably made of metal and plastic respectively, adapted respectively to be secured to the adjacent ends of the femur and the tibia, said femoral component comprising a spaced, joined pair of substantially parallel convex condylar bearing portions, substantially symmetrical with respect to a longitudinal plane, and said tibial component comprising a spaced, joined pair of substantially parallel concave condylar bearing portions, substantially symmetrical with respect to said longitudinal plane, adapted to receive said femoral bearing portions for articulation of the knee in the sagittal plane.

Figure 3:
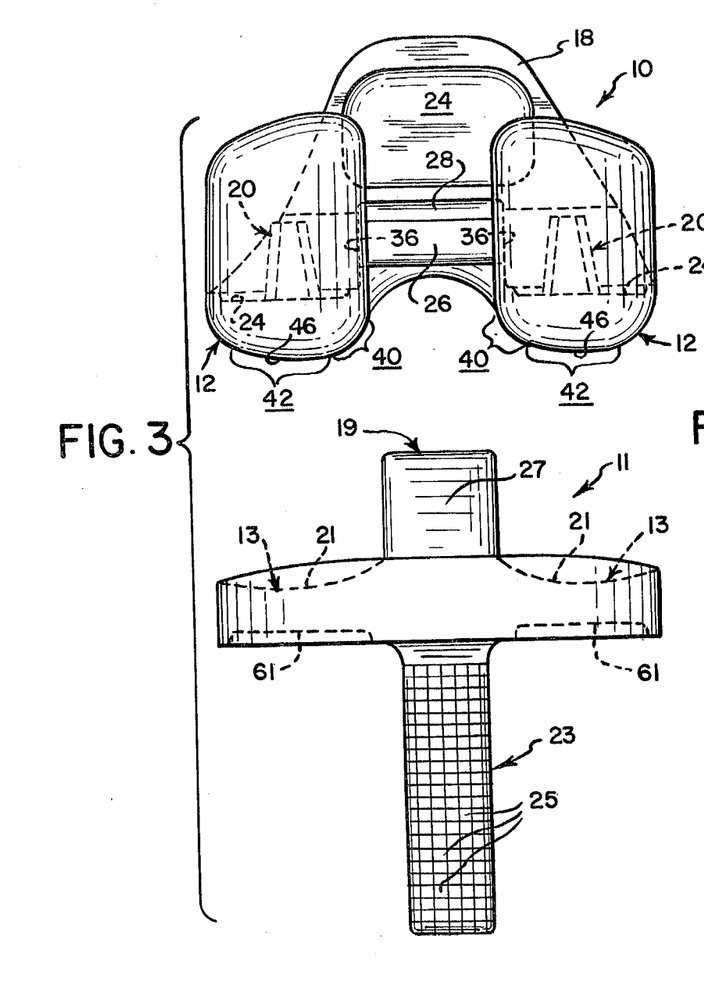
FIG. 3 is an exploded posterior elevation of the prosthesis of FIG. 1.
Figure 4:
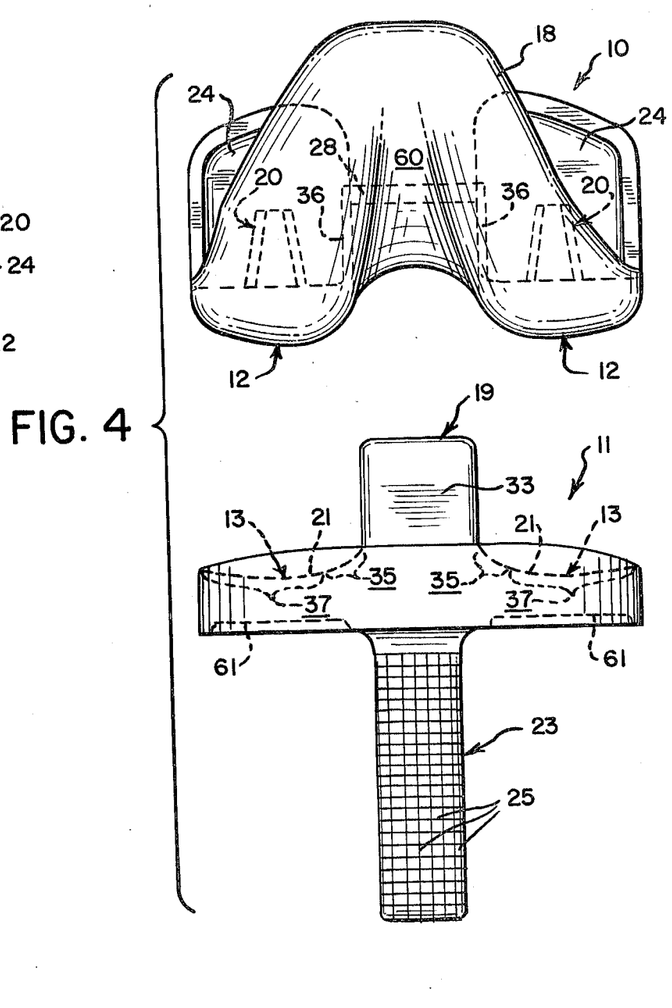
FIG. 4 is an exploded anterior elevation of the prosthesis of FIG. 1.
Figures 5, 6, 7, 8:
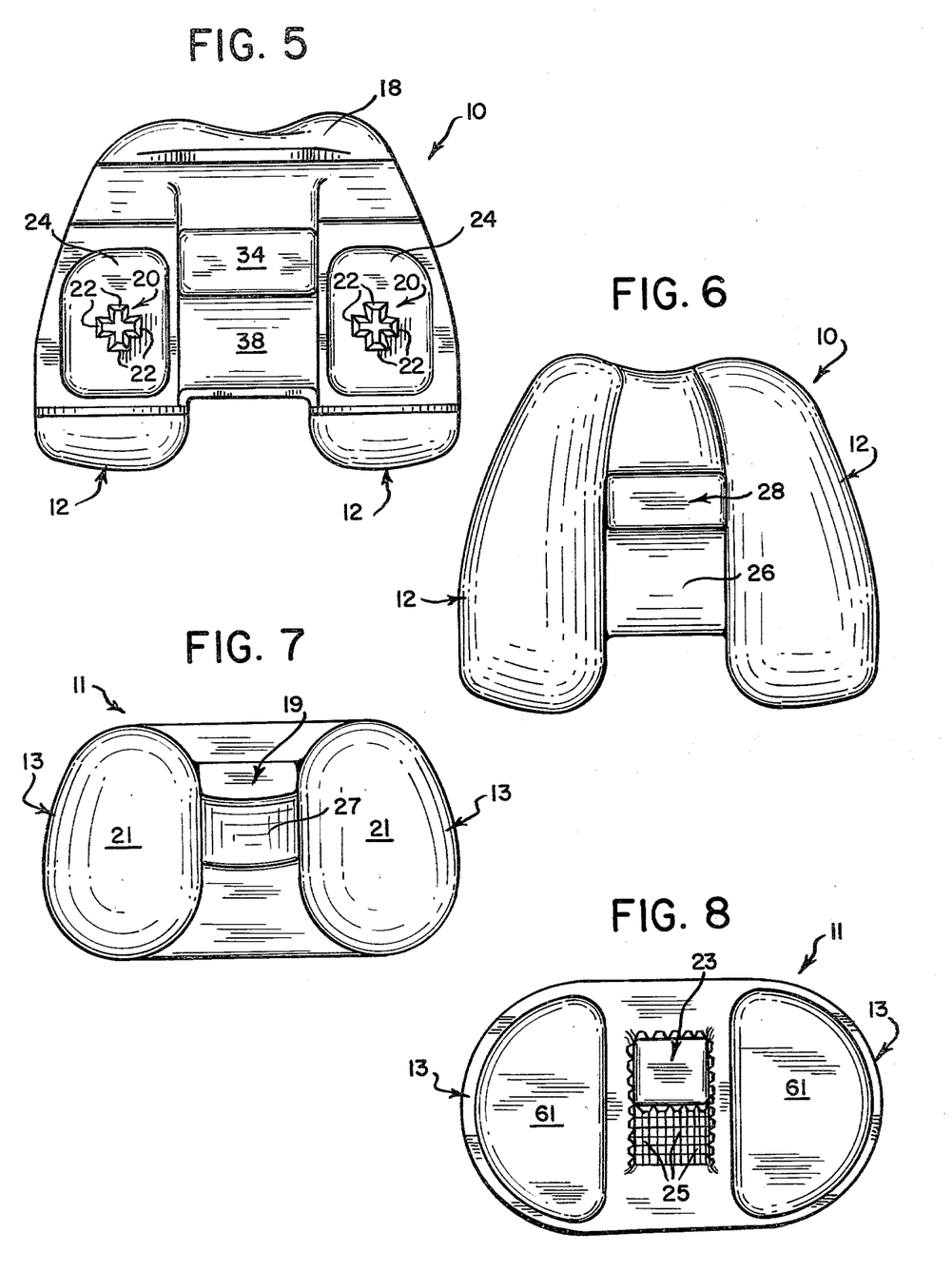
FIG. 5 is a top plan view of the femoral component of the prosthesis of FIG. 1.
FIG. 6 is a bottom plan view of the femoral component of the prosthesis of FIG. 1.
FIG. 7 is a top plan view of the tibial component of the prosthesis of FIG. 1.
FIG. 8 is a bottom plan view of the tibial component of the prosthesis of FIG. 1.
Figure 11:
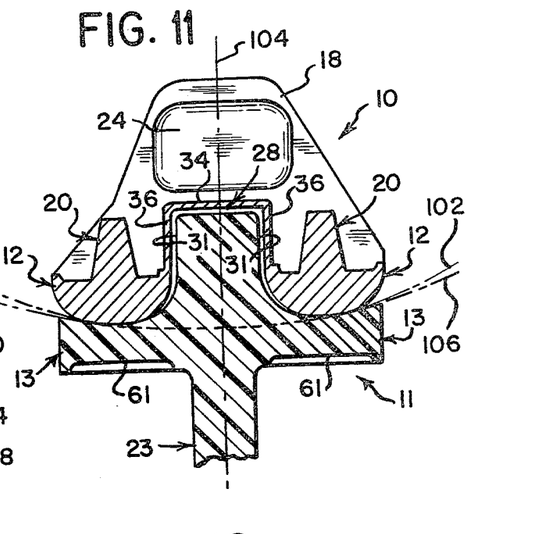
FIG. 11 is a cross-section along line 11—11 of FIG. 9.
Figure 12:
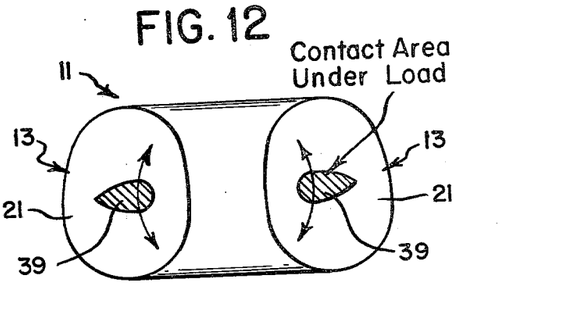
FIG. 12 is a top plan view of the tibial component of the prosthesis of FIG. 1 showing the contact area of the bearing portions and its movement under rotation about a longitudinal axis.

As viewed in FIG. 3 and FIG. 11, each of the bearing surfaces 46 of the femoral bearing portions 12 exhibits an externally convex laterally inner zone 40 and an externally convex laterally outer zone 42 of greater radius of curvature than zone 40. Both of the outer zones 42 are defined in the plane of FIG. 11 (a transverse plane through both portions 12) by different arcs of the same circle 102 of radius $R_F$ centered in the longitudinal plane of symmetry shown as the center line 104 in FIG. 11. Each of the bearing surfaces 21 of the tibial bearing portions 13 exhibits an externally concave laterally inner zone 35 and an externally concave laterally outer zone 37 of greater radius of curvature than zone 35 (FIG. 4). Both of the outer zones 37 are defined in the plane of FIG. 11 (a transverse plane through both portions 13) by different arcs of the same circle 106 of radius $R_T$ centered in the longitudinal plane of symmetry shown in FIG. 11. Finally, $R_F$ and $R_T$ are constant throughout the lengths of femoral and tibial bearing portions 12 and 13 respectively in the anterior/posterior direction, and $R_T$ is slightly greater than $R_F$. The result of this novel configuration is that rotation of the tibial component 11 with respect to the femoral component 10 about the longitudinal axis of the tibia is facilitated by the proximity of the contact area (regions 39 in FIG. 12)

of femoral bearing portions 12 upon tibial bearing portions 13 to the longitudinal axis of the tibia, and the prosthesis is capable of accomodating a few (about plus or minus three) degrees of varus-valgus movements without one of the femoral bearing surfaces 46 lifting above the corresponding tibial bearing surface 21.

As used throughout this application the terms anterior, posterior, up, down, etc. which connote a certain direction refer to the positions of the femoral and tibial components at extension unless the context clearly indicates otherwise.

The femoral and tibial components of knee prostheses according to this invention can be inserted and secured in the body of a patient after removal of deteriorated natural condyles and resection of the extremities of the femur and tibia by methods well known to the art. The two components fit together easily and do not have to be snapped together into mutual engagement.

What is claimed is:

1. A joint prosthesis articulatable between extended and flexed positions comprising a first component, a second component, a bearing portion in each of said components, the bearing portions of said components being in non-linked articulatable mutual contact over a contact area when in use, a guiding surface on each of said components, the guiding surfaces of said components being in mutual contact during at least a major portion of the flexion of said joint from the extended to the flexed position, said guiding surfaces interacting during at least a major portion of the flexion of said joint to effect a corresponding controlled, predetermined, and positive movement of said contact area, and said guiding surfaces being substantially non-load bearing.

2. The device of claim 1 in which the bearing portions of said first component are convex and the bearing portions of said second component are concave.

3. The device of claim 1 in which said joint is the knee, said first component is a femoral component, said second component is a tibial component and the direction of movement of said contact area during flexion is posteriorly.

4. A prosthetic knee joint articulatable between extended and flexed positions comprising a femoral component for securement to the knee end of the femur, a tibial component for securement to the end of the tibia ajdacent to the femur, each of said components having a pair of spaced bearing portions, the bearing portions of said components being in non-linked articulatable mutual contact over a contact area when in use, a post between the pair of bearing portions of one of said components, said post having a guiding surface, said post in use being received between the pair of bearing portions of the other of said components, said other component having a guiding surface between its pair of bearing portions, said guiding surfaces being in mutual contact during at least a major portion of the flexion of said joint from the extended to the flexed positions, and said guiding surfaces interacting during at least a major portion of the flexion of said joint to effect a corresponding controlled, predetermined, and positive posterior movement of said contact area.

5. The device of claim 4 in which said guiding surfaces also interact to prevent anterior movement of the femoral component with respect to the tibial component.

6. The device of claim 5 in which said guiding surfaces are substantially non-load bearing.

7. The device of claim 6 in which each of said post and said other component has a second guiding surface, said second guiding surfaces interacting in the extended position of said knee joint to prevent posterior movement of said femoral component with respect to said tibial component.

8. The device of claim 4 in which said other component is the femoral component, said post is between the bearing portions of the tibial component, and said post is received between the bearing portions of the femoral component.

9. The device of claim 8 in which the guiding surface of said post faces generally posteriorly, and the guiding surface of the femoral component presents a generally convex face to the guiding surface of said post.

10. The device of claim 9 in which the bearing portions of said femoral component has a convex posterior region having a center of curvature, and said convex guiding surface of said femoral component has a center of curvature offset with respect to the center of curvature of said posterior region.

11. The device of claim 10 in which the convex guiding surface of said femoral component is at least a portion of the surface of a circular cylinder, and the longitudinal axis of said cylinder is the center of curvature of the convex guiding surface of the femoral component.

12. The device of claim 11 in which said post has an upper terminus and the guiding surface of said post slopes downwardly and posteriorly from said upper terminus.

13. The device of claim 9 in which the guiding surface of said post is convex in the lateral direction of the joint to facilitate relative rotation between the components about the axis of the tibia when the joint is not extended.

14. The device of claim 9 in which the guiding surface of said post is the anterior surface of an upwardly concave trough, said trough having a posterior wall portion, the convex guiding surface of the femoral component is received in said trough, and the posterior wall portion of said trough prevents posterior dislocation of the femoral component.

15. The device of claim 14 in which said trough is curved, and the curvature of said trough is sufficient to permit said posterior movement of said contact area.

16. A prosthetic knee joint articulatable between extended and flexed positions comprising a femoral component for securement to the knee end of the femur, a tibial component for securement to the end of the tibia adjacent to the femur, each of said components having a pair of spaced bearing portions, each of the pair of bearing portions of said femoral component having a bearing surface, said bearing surfaces being downwardly convex in the lateral direction, said convex bearing surfaces being different arcs of the same first circle, each of the pair of bearing portions of the tibia component being upwardly concave in the lateral direction, said concave bearing surfaces being different arcs of a second circle, and said first mentioned circle having a radius less than the radius of said second circle to insure limited varus-valgus movement of said joint without lifting one of said bearing portions of said femoral component out of bearing contact with its associated bearing portion on the tibial component.

17. A prosthetic knee joint articulatable between extended and flexed positions comprising a femoral component for securement to the knee end of the femur, a tibial component for securement to the end of the tibia adjacent the femur, each of said components having a pair of spaced bearing portions, the bearing portions of said components being in non-linked articulatable mutual contact over a contact area when in use, a post between the pair of bearing portions of one of said components, said post having a guiding surface, said post in use being received between the pair of bearing portions of the other of said components, said other component having a guiding surface between its pair of bearing portions, said guiding surfaces being in mutual contact during at least a portion of the flexion of said joint from the extended to the flexed position, with said guiding surfaces interacting during at least a major portion of the flexion of said joint to effect posterior movement of said contact area, each of the pair of bearing portions of said femoral component having a bearing surface, said bearing surfaces being downwardly convex in the lateral direction, said convex bearing surfaces being different arcs of the same first circle, each of the pair of bearing portions of the tibial component being upwardly concave in the lateral direction, said concave bearing surfaces being different arcs of a second circle, and said first mentioned circle having a radius less than the radius of said second circle to insure limited varus-valgus movement of said joint without lifting one of said bearing portions of said femoral component out of bearing contact with its associated bearing portion on the tibial component.

* * * * *